US012667736B2

(12) United States Patent
Wu et al.

(10) Patent No.: US 12,667,736 B2
(45) Date of Patent: Jun. 30, 2026

(54) HIGH-DOSE-RATE BRACHYTHERAPY WITH OPTIMAL NEEDLE PLACEMENT FOR PROSTATE CANCER

(71) Applicant: University of Iowa Research Foundation, Iowa City, IA (US)

(72) Inventors: Xiaodong Wu, Iowa City, IA (US); Weiyu Xu, Iowa City, IA (US); Jirong Yi, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 776 days.

(21) Appl. No.: 18/170,784

(22) Filed: Feb. 17, 2023

(65) Prior Publication Data

US 2023/0264043 A1      Aug. 24, 2023

Related U.S. Application Data

(60) Provisional application No. 63/312,303, filed on Feb. 21, 2022.

(51) Int. Cl.
*A61N 5/10*          (2006.01)
(52) U.S. Cl.
CPC ......... *A61N 5/1014* (2013.01); *A61N 5/1039* (2013.01)
(58) Field of Classification Search
CPC .. A61N 5/1014; A61N 5/1039; A61N 5/1031; A61N 5/1027; A61N 5/103;
(Continued)

(56) References Cited

U.S. PATENT DOCUMENTS 6,200,255 B1 *   3/2001   Yu ........................ A61N 5/1031
                                                                    600/3
10,933,254 B2 *   3/2021   Borot De Battisti ......................
                                                                    A61N 5/1027
(Continued)

FOREIGN PATENT DOCUMENTS

WO        WO-2017037060 A1 *   3/2017   ........... A61N 5/1027

OTHER PUBLICATIONS

Akimoto T, Katoh H, Noda SE, et al. Acute genitourinary toxicity after high dose rate (HDR) brachytherapy combined with hypofractionated external-beam radiation therapy for localized prostate cancer: second analysis to determine the correlation between the urethral dose in HDR brachytherapy and the severity of acute genitourinary toxicity. Int J Radiat Oncol Biol Phys. 2005; 63: 472-478.
(Continued)

*Primary Examiner* — Brian L Casler
(74) *Attorney, Agent, or Firm* — Goodhue, Coleman & Owens, P.C.

(57)          ABSTRACT
A method for needle position optimization for prostate brachytherapy for use with a radiation delivery device configured to use a plurality of needles inserted into a prostate of a patient includes obtaining imagery of the prostate of the patient, generating a needle pool for prostate brachytherapy treatment of the patient based on the imagery of the prostate of the patient, and determining at a computing device an optimum prostate brachytherapy treatment plan for the patient by iteratively removing needles from the needle pool by forming and computationally solving a convex optimization problem wherein the convex optimization problem uses a quadratic dosimetric penalty function, dwell time regularization by total variation, and block sparsity regularization term.

18 Claims, 7 Drawing Sheets
(5 of 7 Drawing Sheet(s) Filed in Color)

(58) Field of Classification Search

CPC ............... A61N 5/1071; A61N 5/1007; A61N 2005/1012; A61N 5/1037; A61N 5/1064; A61N 5/1001; A61B 5/055; A61B 34/10; A61B 2034/102; A61B 2034/104; A61B 2034/101; A61B 2034/105; A61B 2034/107; A61B 2034/108; G16H 20/40; G16H 40/63; G16H 50/50; G16H 50/30; G01T 1/02; G01T 1/2914

USPC ...................... 600/300, 411, 416, 424, 427, 3

See application file for complete search history.

(56) References Cited

U.S. PATENT DOCUMENTS

| | | | | |
|---|---|---|---|---|
| 2011/0091014 A1* | 4/2011 | Siljamaki | ............. | A61N 5/1031 |
| | | | | 378/65 |
| 2012/0089008 A1* | 4/2012 | Strehl | .................. | G01R 33/286 |
| | | | | 600/411 |
| 2015/0367144 A1* | 12/2015 | Flynn | ................... | A61N 5/1031 |
| | | | | 600/7 |
| 2017/0036037 A1* | 2/2017 | Luan | ..................... | A61N 5/1031 |
| 2019/0255355 A1* | 8/2019 | Nordström | ........... | A61N 5/1071 |
| 2020/0075151 A1* | 3/2020 | Long | .................... | A61N 5/1031 |

OTHER PUBLICATIONS

Famulari G, Duclos M, Enger SA. A novel 169 Yb-based dynamic-shield intensity modulated brachytherapy delivery system for prostate cancer. Med Phys. Mar. 2020;47(3):859-868.

Ferrari G, Kazareski Y, Laca F, Testuri CE. A model for prostate brachytherapy planning with sources and needles position optimization. Operations Research for Health Care. Mar. 1, 2014;3(1):31-9.

Fougner C, Boyd S. Parameter selection and preconditioning for a graph form solver. InEmerging Applications of Control and Systems Theory 2018 (pp. 41-61). Springer, Cham.

Gomez-Iturriaga A, Casquero F, Pijoan JI, et al. Health-related-quality-of-life and toxicity after single fraction 19 Gy high-dose-rate prostate brachytherapy: Phase II trial. Radiother Oncol. 2017; 26: 278-282.

Le A, Yi J, Kim Y, Flynn R, Xu W, Wu X. Keyway selection optimization for multi-helix rotating shield brachytherapy (H-RSBT). Medical Physics. 2018;45(6):E159-E159.

Martinez AA, Gonzalez J, Ye H, et al. Dose escalation improves cancer-related events at 10 years for intermediate- and high-risk prostate cancer patients treated with hypofractionated high-dose-rate boost and external beam radiotherapy. Int J Radiat Oncol Biol Phys. 2011; 79: 363- 370.

Mohammed N, Kestin L, Ghilezan M, et al. Comparison of acute and late toxicities for three modern high-dose radiation treatment techniques for localized prostate cancer. Int J Radiat Oncol Biol Phys. 2012; 82: 204-212.

Morton G, McGuffin M, Chung HT, Tseng CL, Helou J, Ravi A, Cheung P, Szumacher E, Liu S, Chu W, Zhang L. Prostate high dose-rate brachytherapy as monotherapy for low and intermediate risk prostate cancer: Efficacy results from a randomized phase II clinical trial of one fraction of 19 Gy or two fractions of 13.5 Gy. Radiotherapy and Oncology. 2020;146:90-6.12.

Prada PJ, Cardenal J, Blanco AG, et al. High-dose-rate interstitial brachytherapy as monotherapy in one fraction for the treatment of favorable stage prostate cancer: Toxicity and long-term biochemical results. Radiother Oncol. 2016; 119: 411-416.

Siauw T, Cunha A, Berenson D, Atamtürk A, Hsu IC, Goldberg K, Pouliot J. NPIP: A skew line needle configuration optimization system for HDR brachytherapy. Medical physics. Jul. 2012;39(7Part1):4339-46.

Siddiqui ZA, Gustafson GS, Ye H, Martinez AA, Mitchell B, Sebastian E, Limbacher A, Krauss DJ. Five-year outcomes of a single-institution prospective trial of 19-Gy single-fraction high-dose-rate brachytherapy for low-and intermediate-risk prostate cancer. International Journal of Radiation Oncology* Biology* Physics. 2019; 104(5):1038-44.

Sullivan L, Williams SG, Tai KH, Foroudi F, Cleeve L, Duchesne GM. Urethral stricture following high dose rate brachytherapy for prostate cancer. Radiotherapy and Oncology. 2009;91(2):232-236.

Wang C, Gonzalez Y, Shen C, Hrycushko B, Jia X. Simultaneous needle catheter selection and dwell time optimization for preplanning of high-dose-rate brachytherapy of prostate cancer. Physics in Medicine & Biology. Feb. 26, 2021;66 (5):055028.

Yi J, Wu X, Adams Q, Hopfensperger K, Patwardhan K, Flynn R, Kim Y, Xu W. Optimized rotating shield brachytherapy treatment plan under treatment time budget. Medical Physics. Jun. 2019;46(6):E562-E562.

Yoshioka Y, Suzuki O, Isohashi F, et al. High-dose-rate brachytherapy as monotherapy for intermediate- and high-risk prostate cancer: clinical results for a median 8-year follow-up. Int J Radiat Oncol Biol Phys. 2016; 94: 675-682.

Adams Q, Hopfensperger KM, Kim Y, et al. Effectiveness of rotating shield brachytherapy for prostate cancer dose escalation and urethral sparing. Int J Radiat Oncol Biol Phys. 2018; 102: 1543-1550.

Adams Q, Hopfensperger KM, Kim Y, Wu X, Flynn RT. 169Yb-based rotating shield brachytherapy for prostate cancer. Medical Physics. Dec. 2020;47(12):6430-9.

Cho M, Wu X, Dadkhah H, Yi J, Flynn RT, Kim Y, Xu W. Fast dose optimization for rotating shield brachytherapy. Medical Physics. Oct. 2017;44(10):5384-92.

Dadkhah H, Hopfensperger KM, Kim Y, Wu X, Flynn RT. Multisource rotating shield brachytherapy apparatus for prostate cancer. Int J Radiat Oncol Biol Phys. 2017; 99: 719-728.

Flynn RT, Adams QE, Hopfensperger KM, Wu X, Xu W, Kim Y. Efficient (169) Yb high-dose-rate brachytherapy source production using reactivation. Med Phys. 2019; 46: 2935-2943.

Heemsbergen WD, Al-Mamgani A, Slot A, Dielwart MF, Lebesque JV. Long-term results of the Dutch randomized prostate cancer trial: impact of dose-escalation on local, biochemical, clinical failure, and survival. Radiother Oncol. 2014; 110: 104-109.

Hindson BR, Millar JL, Matheson B. Urethral strictures following high-dose-rate brachytherapy for prostate cancer: Analysis of risk factors. Brachytherapy. 2013;12(1):50-55.

Isu IC, Hunt D, Straube W, et al. Dosimetric analysis of radiation therapy oncology group 0321: the importance of urethral dose. Pract Radiat Oncol. 2014; 4: 27-34.

Kuban DA, Tucker SL, Dong L, et al. Long-term results of the M. D. Anderson randomized dose-escalation trial for prostate cancer. Int J Radiat Oncol Biol Phys. 2008; 70: 67-74.

Liu J, Kaidu M, Sasamoto R, Ayukawa F, Yamana N, Sato H, Tanaka K, Kawaguchi G, Ohta A, Maruyama K, Abe E. Two-fraction high-dose-rate brachytherapy within a single day combined with external beam radiotherapy for prostate cancer: single institution experience and outcomes. Journal of radiation research. Jun. 1, 2016;57(3):280-287.

Liu Y, Flynn RT, Kim Y, Dadkhah H, Bhatia SK, Buatti JM, Xu W, Wu X. Paddle-based rotating-shield brachytherapy. Medical Physics. Oct. 2015;42(10):5992-6003.

Liu Y, Flynn RT, Kim Y, Yang W, Wu X. Dynamic rotating-shield brachytherapy. Medical Physics. Dec. 2013;40(12):121703.

Liu Y, Flynn RT, Yang W, Kim Y, Bhatia SK, Sun W, Wu X. Rapid emission angle selection for rotating-shield brachytherapy. Medical Physics. May 2013;40(5):051720.

Siegel RL, Miller KD, Fuchs HE, Jemal A. Cancer statistics, 2022. CA: a Cancer Journal for Clinicians.2022;71(1):7-33.

Van der Meer MC, Pieters BR, Niatsetski Y, Alderliesten T, Bel A, Bosman PA. Better and faster catheter position optimization in HDR brachytherapy for prostate cancer using multi-objective real-valued GOMEA. InProceedings of the Genetic and Evolutionary Computation Conference Jul. 2, 2018 (pp. 1387-1394).

* cited by examiner

HIGH-DOSE-RATE BRACHYTHERAPY WITH OPTIMAL NEEDLE PLACEMENT FOR PROSTATE CANCER

RELATED APPLICATIONS

This application claims priority to U.S. Provisional Patent Application, 63/312,303, filed Feb. 21, 2022, entitled High-Dose-Rate Brachytherapy with Optimal Needle Placement for Prostate Cancer, hereby incorporated by reference in its entirety.

FEDERALLY SPONSORED RESEARCH AND DEVELOPMENT

This invention was made with government support under R01 EB020665 awarded by the National Institutes of Health. The government has certain rights in the invention.

FIELD OF THE INVENTION

The present invention relates to prostate cancer treatment. More particularly, but not exclusively, the present invention relates to treatment planning which provides for optimizing needle position used in brachytherapy for prostate cancer patients.

BACKGROUND

Prostate cancer is the most prevalent non-skin cancer among men in the United States. Multi-fraction high-dose-rate brachytherapy (HDR-BT) is a localized prostate cancer treatment technique with high efficacy. In brachytherapy, placing a radiation source inside or directly adjacent to the target tissue allows for delivering a focused dose of radiation to the target tissue with relatively low dosages of radiation being delivered to surrounding or intervening healthy tissues and nearby organs at risk. High-dose rate has been generally viewed as effective especially when provided in multiple fractions. However, the placement of needles holding radiation sources plays a critical role in determining the quality of prostate HDR-BT treatment plans. Traditional treatment planning optimization techniques have used needle locations based on physician-manually-and-empirically-defined templates. This process of manually determining the locations of needle locations and the dwell time at each location was time-and-labor consuming, and results in needle locations that are not optimal for treatment. This disclosure presents a novel prostate HDR-BT treatment planning method, which enables automated needle position optimization, thus achieving personalized precision brachytherapy for prostate cancer patients.

SUMMARY

Therefore, it is a primary object, feature, or advantage to improve over the state of the art.

It is a further object, feature, or advantage to provide for improved treatment planning for brachytherapy.

It is a still further object, feature, or advantage to provide for automated needle position optimization.

It is another object, feature, or advantage to provide for determination of needle dwell time at each location in brachytherapy treatment.

It is yet another object, feature, or advantage to provide better patient outcomes from personalized precision brachytherapy for prostate cancer patients.

One or more of these and/or other objects, features, or advantages will become apparent from the specification and claims that follow. No single embodiment need meet or exhibit each and every one of these objects, features, or advantages as different embodiments may have different objects, features, or advantages whether stated herein or not. Thus, the claimed invention is not to be limited by or to these objects, features, or advantages.

According to one aspect, a method for needle position optimization for prostate brachytherapy for use with a radiation delivery device configured to use a plurality of needles inserted into a prostate of a patient is provided. The method includes obtaining imagery of the prostate of the patient, generating a needle pool for prostate brachytherapy treatment of the patient based on the imagery of the prostate of the patient, and determining at a computing device an optimum prostate brachytherapy treatment plan for the patient by iteratively removing needles from the needle pool by forming and computationally solving a convex optimization problem wherein the convex optimization problem uses a quadratic dosimetric penalty function, dwell time regularization by total variation, and block sparsity regularization term. The method may further include performing the prostate brachytherapy according to the optimum prostate brachytherapy treatment plan for the patient. The imagery may be magnetic resonance imagery such as may be obtained with a portable magnetic resonance imaging (MRI) scanner. The prostate brachytherapy may be prostate rotating shield brachytherapy (RSBT) or high-dose-rate brachytherapy (HDR-BT).

According to another aspect, a radiation treatment planning system for prostate brachytherapy for use with a radiation delivery device configured to use a plurality of needles inserted into a prostate of a patient is provided. The system includes a processor, a memory operatively connected to the processor having instructions stored thereon for execution by the processor to: obtain imagery of the prostate of the patient; generate a needle pool for prostate brachytherapy treatment of the patient based on the imagery of the prostate of the patient; determine an optimum prostate brachytherapy treatment plan for the patient by iteratively removing needles from the needle pool by forming and computationally solving a convex optimization problem wherein the convex optimization problem uses a quadratic dosimetric penalty function, dwell time regularization by total variation, and block sparsity regularization term. The instructions may further provide for generating an output in a human-readable form conveying the optimum prostate brachytherapy treatment plan for the patient.

According to another aspect, a system for prostate brachytherapy is provided which includes a plurality of needles, a radiation delivery device configured to use the plurality of needles when inserted into a prostate of a patient to delivery radiation thereto, a processor, and a memory operatively connected to the processor having instructions stored thereon for execution by the processor to: obtain imagery of the prostate of the patient; generate a needle pool for prostate brachytherapy treatment of the patient based on the imagery of the prostate of the patient; and determine an optimum prostate brachytherapy treatment plan for the patient by iteratively removing needles from the needle pool by forming and computationally solving a convex optimization problem wherein the convex optimization problem uses a quadratic dosimetric penalty function, dwell time regularization by total variation, and block sparsity regularization term.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Illustrated embodiments of the disclosure are described in detail below with reference to the attached drawing figures.

FIG. 3A and FIG. 3B are obtained under the urethra sparing goal, while FIG. 3C and FIG. 3D are obtained under the dose escalation goal. FIG. 3A and FIG. 3C are obtained when only programmatic needles are used for selection while FIG. 3B and FIG. 3D are obtained when both clinical and programmatic needles are used for selection. The 'R' and 'H' refer to the RSBT and HDR-BT baselines without needle selection, respectively.

DETAILED DESCRIPTION

I. Overview and Introduction

Figure 1:
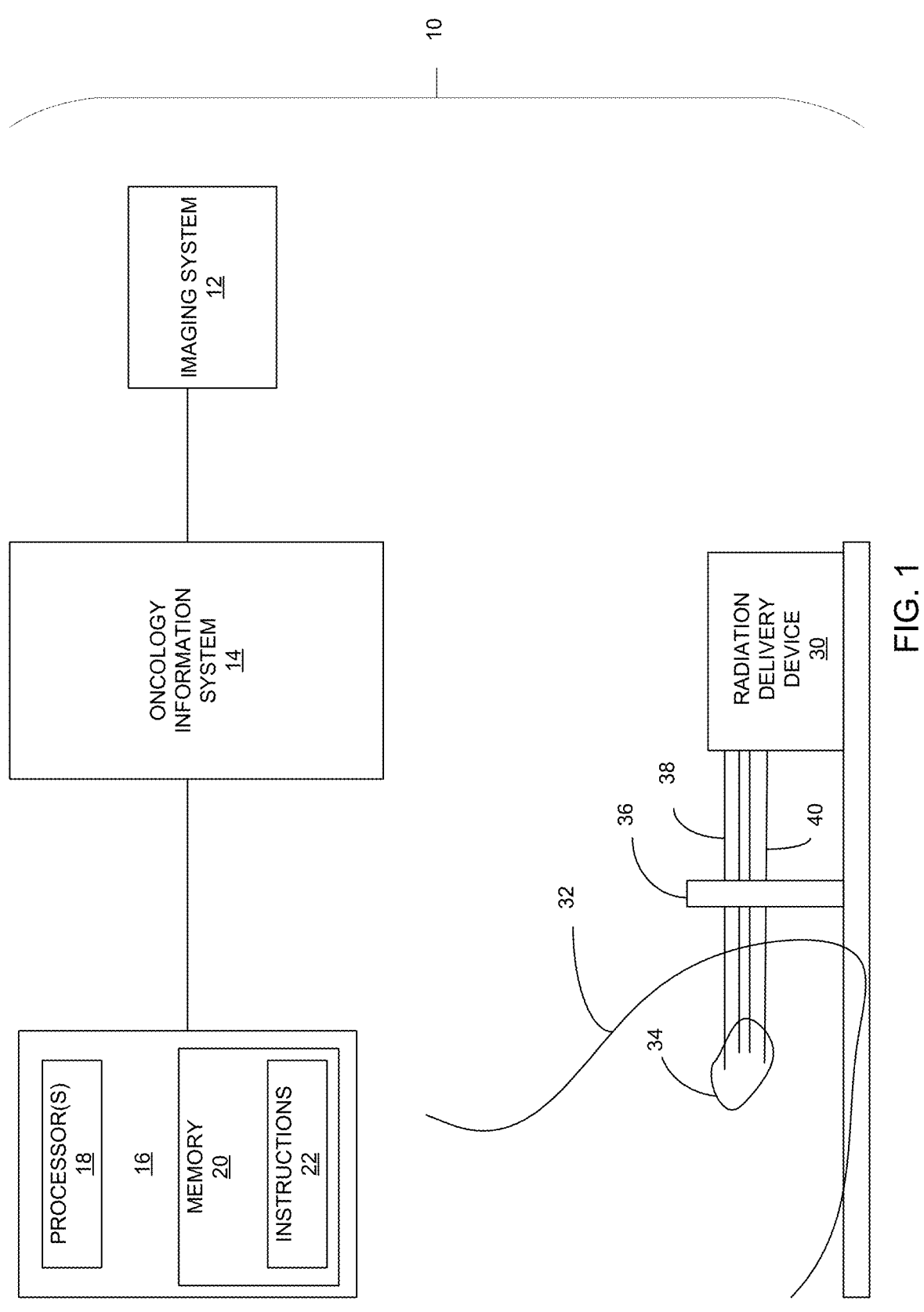
FIG. 1 is an overview of a system for prostate brachytherapy.

FIG. 1 provides an overview of one example of a system associated with brachytherapy. In FIG. 1 a system 10 is shown. The system 10 includes an imaging system 12 which may be used to acquire biomedical imagery. The imaging system 12 may be of any number of different types. For example, in one embodiment the imaging system 12 is a magnetic resonance imaging (MRI) scanner such as a portable MRI scanner. Alternatively, the imaging system 12 may be a computed tomography (CT) type scanner or other imaging system. The imaging system 12 may be used to acquire images needed for treatment planning. Imagery acquired with the imaging system 12 may be communicated to an oncology information system 14. The oncology information system 14 may include a computing device and a storage media to provide for storing the imagery or other data such as on a non-transitory computer readable storage media. A treatment planning system 16 is operatively connected to the oncology information system 14. The treatment planning system 16 may include a computing device with one or more processors 18 and a memory 20 in operative communication with the one or more processors 18. The memory may be a non-transitory computer readable storage medium and may have a set of instructions 22 stored thereon for execution by the one or more processors 18. The instructions 22 may implement one or more of the methodologies described herein in order to generate a treatment plan, especially a treatment plan for prostate cancer which optimizes needle position used in brachytherapy such as HDR-BT and/or RSBT.

The system 10 may include a radiation delivery device 30 which may be used to provide radiation through needles such as needles 38, 40. As used herein, the term needles may also encompass catheters, guide tubes, or other elements. The needles 38, 40 may be inserted through a template 36 and into the prostate 34 of a patient 32. The template 36 is fixed relative to the prostate 34 of the patient 32. The template 36 may have a grid layout to provide a number of potential needle positions. The system 10 may further include an imaging probe (not shown) used to acquire imagery of the patient during the procedure.

The treatment planning system 16 may provide for determination of an optimal number and position a set of needles as well as dwell times of energy emitting source used to deliver radiation.

Figure 2:
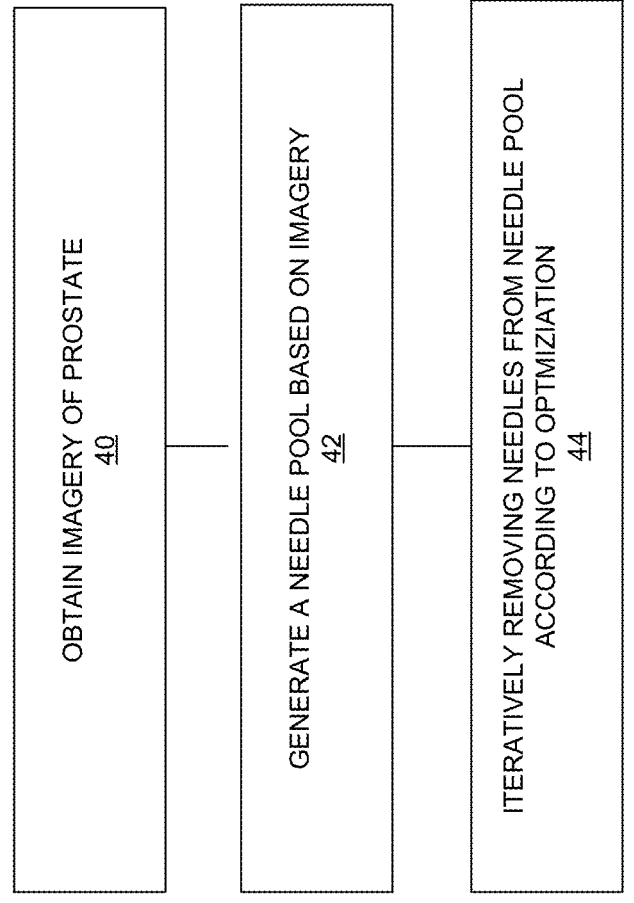
FIG. 2 illustrates one example of a method for prostate brachytherapy planning.
Figure 3A:
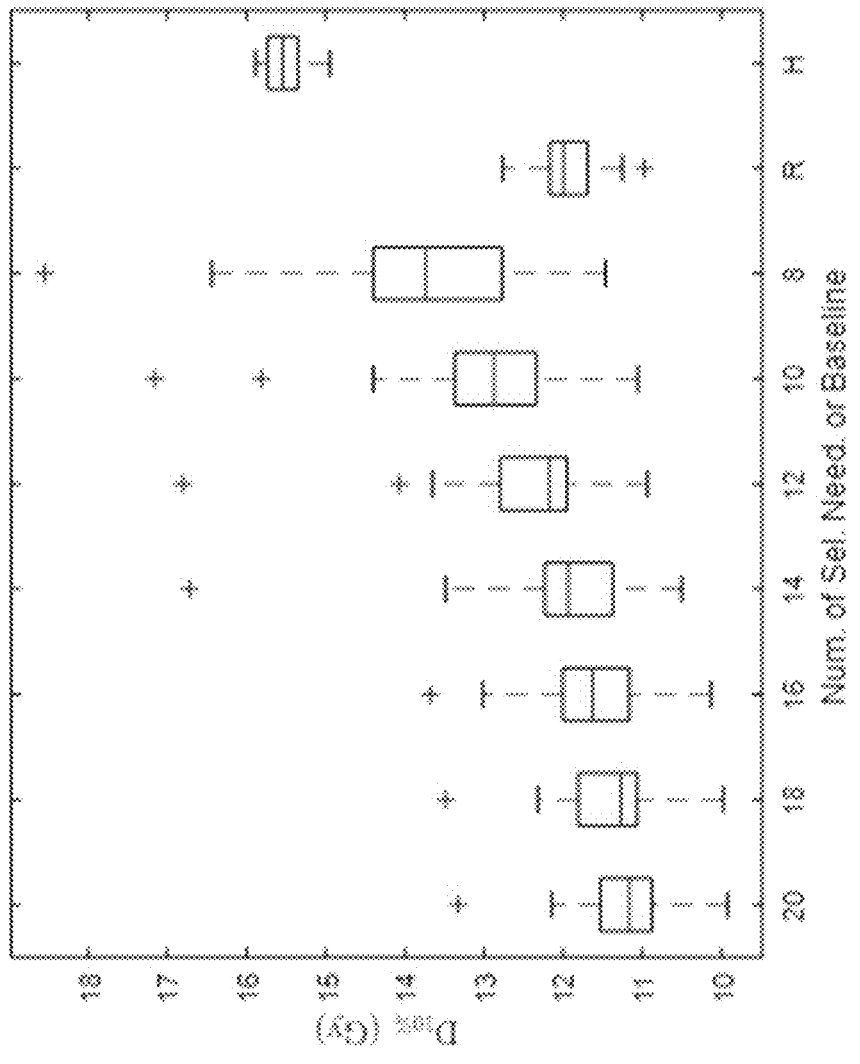
FIGS. 3A, 3B, 3C, and 3D are a set of boxplots of the urethra $D_{10\%}$ and the PTV $D_{90\%}$.
Figure 3B:
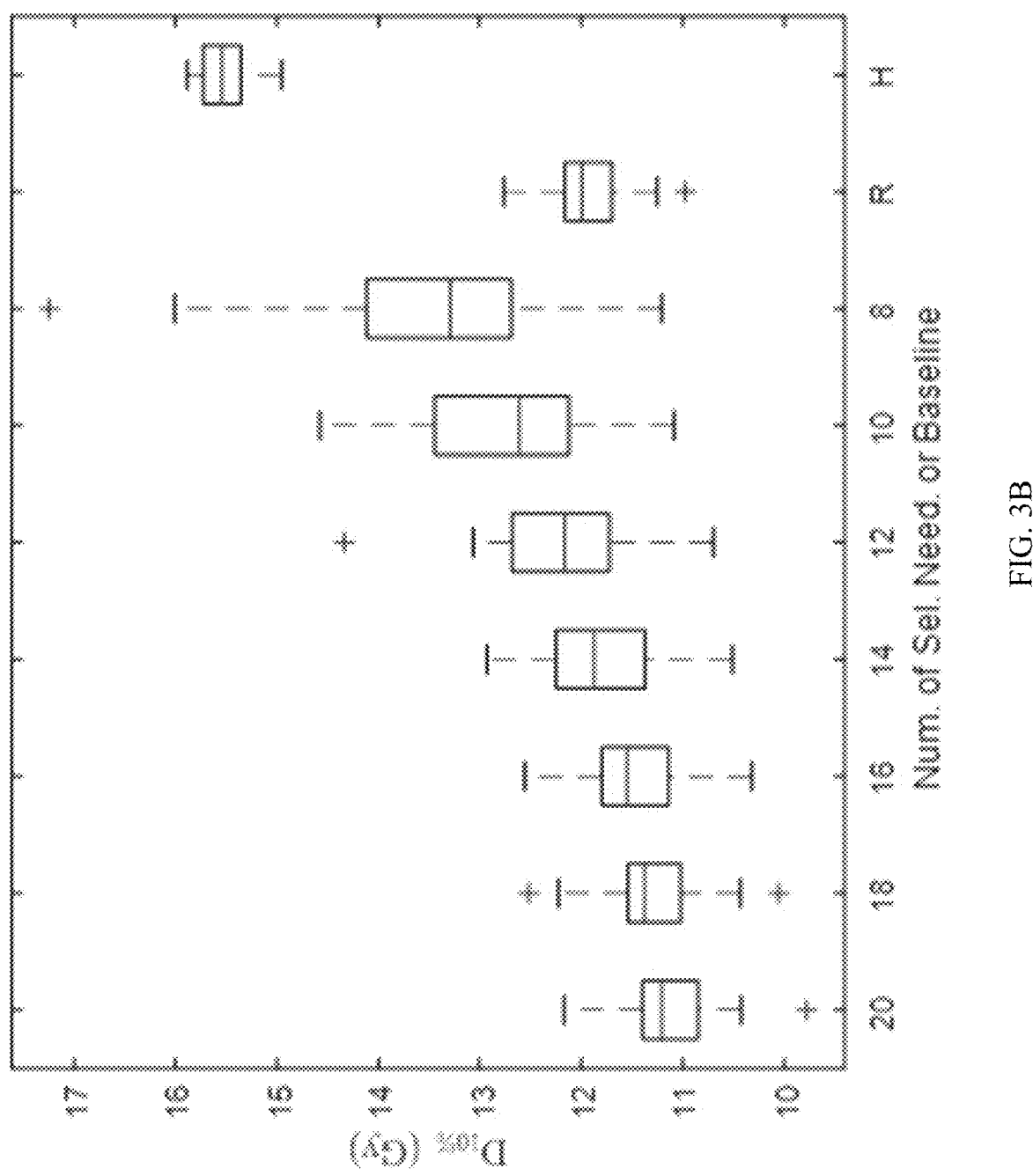
Figure 3C:
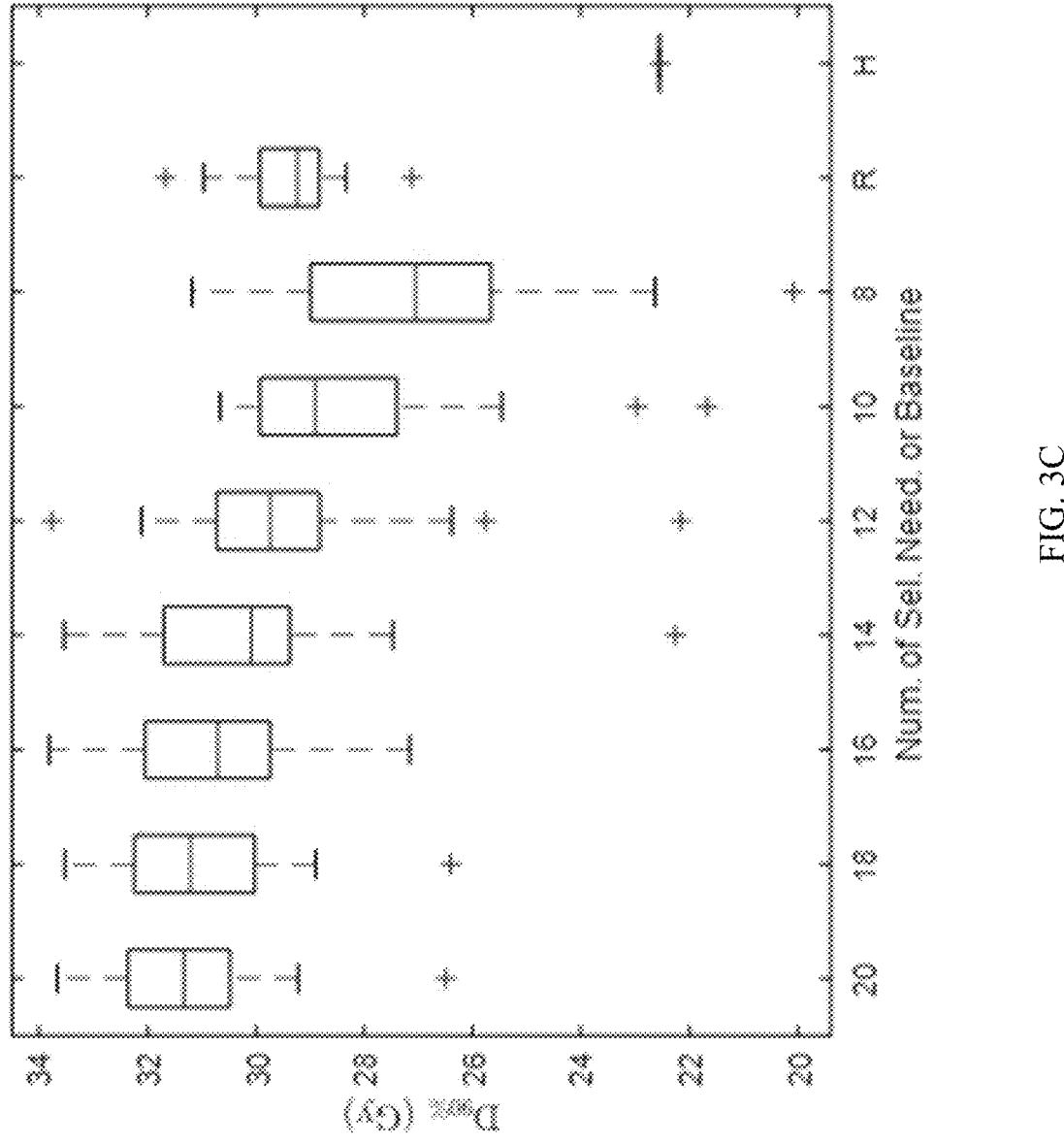
Figure 3D:
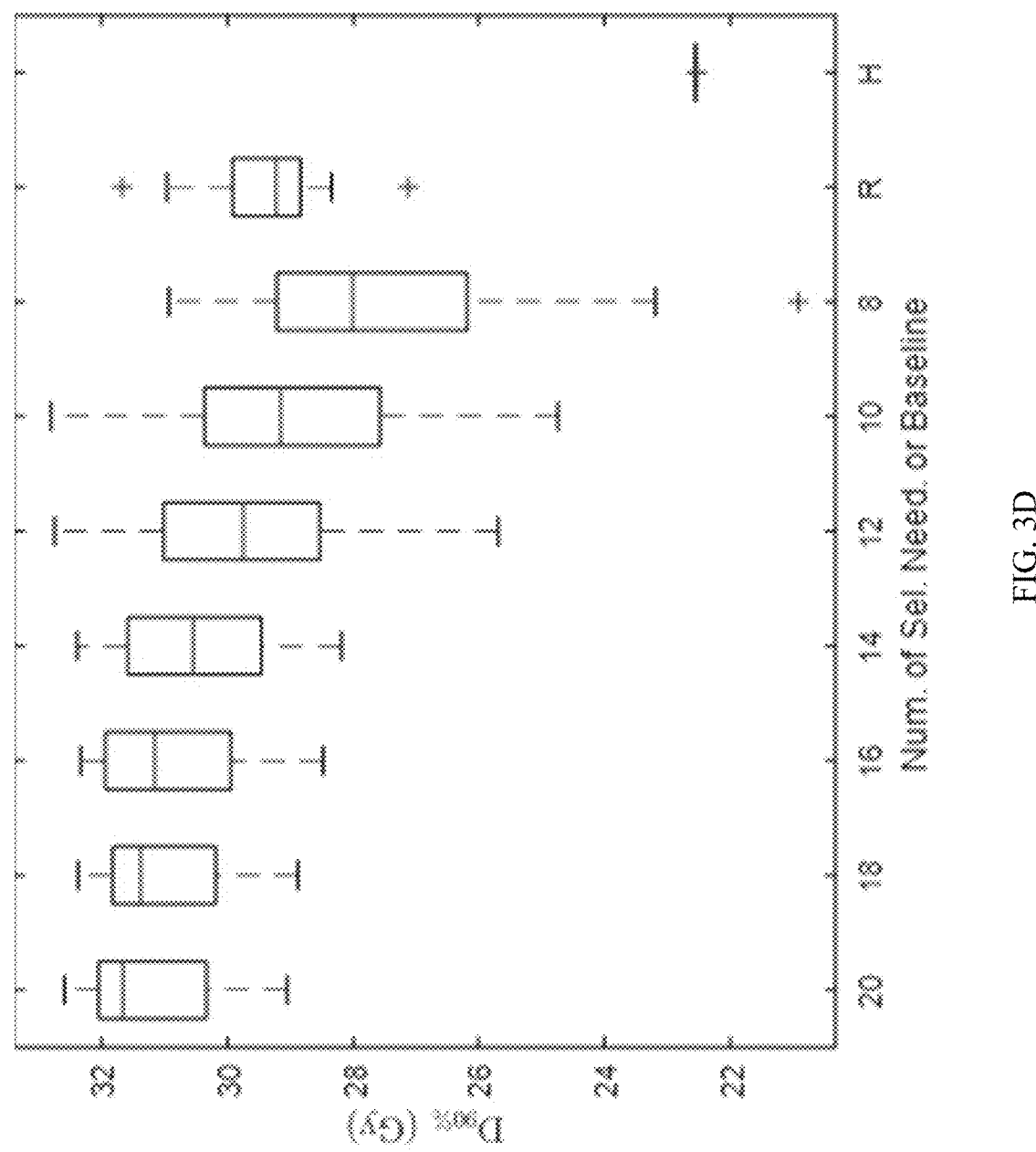

FIG. 2 is an overview of one method shown and described. In step 40, imagery of a prostate is obtained. This imagery may be acquired from an imaging device such as an MRI device, a CT device, or other type of imaging device. In step 42, a needle pool is generated at least partially based on the imagery of the prostate. Then in step 44, an optimization problem is solved which provides for iteratively removing needles from the needle pool to result in a treatment plan.

As previously mentioned, prostate cancer is the most prevalent non-skin cancer among men in the United States.[1] Multi-fraction high-dose-rate brachytherapy (HDR-BT) is a localized prostate cancer treatment technique to achieve high biochemical control rates and low toxicity.[2] Due to the desire to reduce the number of needle implants and improve convenience for patients, single-fraction HDR-BT has been proposed, however, biochemical control rates for single-fraction HDR-BT have been substandard.[3,4,5] It is possible that biochemical control rates can be improved when the dose received by the planning target volume (PTV) is escalated given evidence of the effectiveness of dose escalation in treating prostate cancer.[6,7,8,9] The level of dose escalation achievable, however, is limited by the dose delivered to nearby organs at risk, especially the urethra.[10,11,12] For HDR-BT, the dose delivered to urethra can result in an increase in the risk of Grade 2 or higher GU toxicity and a decrease in the Expanded Prostate Index Composite urinary domain score.[10,13,14,15] This motivates the introduction of rotating shield brachytherapy (RSBT) for prostate cancer, which enables dose escalation to the planning target volume (PTV), urethra dose reduction, or both.[16,17,18]

To deliver RSBT for prostate cancer, a $^{169}$Yb source and delivery system was proposed to enable clinically practical delivery times with a commercially feasible isotope,[17,19] while an $^{192}$Ir source is widely used for HDR-BT in general. The mathematical models for HDR-BT/RSBT treatment planning have usually been formulated as an optimization problem either in discrete form or continuous form, the optimization solvers also have developed correspondingly with combinatorial optimization or convex optimization.[20,21,22,23,24]

The placement or location of needles plays a critical role in determining the quality of prostate HDR-BT and RSBT treatment plans, with quality metrics including the maximally achievable PTV $D_{90\%}$ and the operational complexity such as the minimum number of needles required to achieve a certain PTV $D_{90\%}$ goal. Previously-proposed optimization techniques have used needle locations based on empirically-defined templates, resulting in needle locations that are feasible but not necessarily optimal for treatment planning.[17,25] In this work, an algorithm for optimizing the selection of needles for prostate HDR-BT/RSBT is proposed, motivated by the desire for the highest possible PTV $D_{90\%}$ under the dose escalation goal or the lowest possible urethra $D_{10\%}$ under the urethra sparing goal. It is also desirable to minimize the number of needles for achieving a dosimetric goal. The proposed method is exemplified on prostate RSBT treatment planning. Our approach demonstrates the potential for improving upon previous approaches.[22,26,27,28] Concurrently, Wang et al. considered similar needle selection problem for traditional prostate HDR-BT (not RSBT, based on the $^{192}$Ir isotope), using a different algorithm to solve the problem.[29]

II. Materials and Methods

II.A Treatment Planning

Twenty-six anonymous prostate cancer patients were considered, which were previously treated with HDR-BT. The same procedures for implementation of catheter and treatment planning as introduced by Adams et al. were followed after the optimal needles are selected.[17] The HDR-BT treatment plans were generated assuming a 10 Ci [192]Ir Varian VariSource (Varian Medical Systems, Inc., Palo Alto, CA) radiation source, and the RSBT treatment plans were generated assuming a re-activatable 27 Ci [169]Yb source.[19] The source activities were selected to ensure they both had the same dose rate in water at 1 cm off axis when unshielded. The same approach for dose delivery was assumed in the current work except that a needle selection technique was applied to select optimal needles for treatment planning.[17] Specifically, we use RSBT with NEEdle Position Optimization (NEEPO) to first select a set of optimal needles, and then use this set of optimal needles to generate optimal treatment plans. The key idea of generating treatment plans using the optimally selected needles is to solve a convex optimization problem where the objective function involves two terms, one for quantifying the difference between the generated treatment plan and the prescribed treatment plans, and the other for encouraging the smoothness of dose delivery.[17] The treatment plans obtained via RSBT NEEPO will then be compared with those obtained by using RSBT or HDR-BT only.

II.B. Treatment Planning with Optimized Needle Selection

The NEEPO algorithm begins by generating a pool of needle positions from which optimized needle selection will be performed. To accomplish this, the maximum axial projection was first sampled at the original resolution as the initial image set which may be a CT image set, MRI image set, or other image set. This image is then down-sampled into a 5 mm by 5 mm grid to reflect needle density constraints imposed on implantation of needles by commonly used prostate brachytherapy templates. Each down-sampled pixel position was defined as a potential programmatically generated needle position. Clinical needle positions were not considered as potential programmatic needle positions, as they instead form a clinical needle set. The set of dwell positions for clinical needles were sampled and the clinical needle with the most dwell positions was used as a basis needle to generate the dwell positions for each programmatic needle. The basis needle was assigned to each potential needle position by a linear shift, and the dwell positions from this basis needle were used for all the other needles. The PTV was decomposed into 4 quadrants of equal area on the maximum axial projection slice and the generated needles were each assigned to a quadrant.

Once the needle pool has been constructed, an optimization problem with block sparsity regularization is solved to determine the optimal set of needles to use. It is possible to preset the number of needles to be selected, k, and in this case, we can simply take the k needles with the most dwell time after accounting for needle removal/redistribution as described in detail in this section. Once the optimal set of needles is selected, those needles are used to formulate a treatment planning optimization,[20] and solving this optimization problem will provide an optimal treatment plan with the optimally selected needles. We will evaluate the effects of needle selection primarily for RSBT with both the dose escalation goal and the urethra sparing goal. We will evaluate the needle selection techniques in two different scenarios: one where only the programmatic needles are for selection (clinical needles are excluded), and the other where both the clinical needles and the programmatic needles are used for selection.

In this section, we will formulate the needle selection as a convex optimization, and by solving it, we can decide which of the candidate needles should be used for treatment planning.

(1) Optimal Needle Selection via Block Sparsity

Assume there are a total $p \in Z$ needles in needle pool for selection, and there are n dwell positions for each needle. We now denote the dose rate matrix for the u-th needle by $D[u] \in \mathcal{R}^{m \times n}$ where m is the number of voxels of interest (VOIs), and the i-th row of D[u] represents the dose rate for the i-th VOI due to the source from the u-th needle at different dwell positions. Then the dose rate matrix for all needles at all potential dwell positions can be written as $D=[D[1] \ D[2] \ldots D[p]] \in \mathcal{R}^{m \times np}$. Define $t=[t[1]^T t[2]^T \ldots t[p]^T \in \mathcal{R}^{np}$ where each $t[u] \in \mathcal{R}^n$ is the delivery time vector of the u-th needles at the corresponding n dwell positions, and we can compute the dose for all VOIs $d \in R^m$ as d=Dt.

We propose to achieve optimal needle selection by solving $$\min_{d,t} h(d) + \beta \|t\|_{TV} + \gamma \|t\|_{2,1} \ \text{s.t.} \ Dt = d, t \geq 0, \tag{1}$$

Where the $\beta > 0$ and the $\gamma > 0$ are two positive regularization parameters. The function $h(d):R^m \rightarrow R$ is defined as $$h(d) = \sum_{i=1}^{m} \left( \lambda_i^+ H(d_i - \hat{d}_i) + \lambda_i^- H(\hat{d}_i - d_i) \right)(d_i - \hat{d}_i)^2 \tag{2}$$

Where $$\lambda_i^+ \geq 0$$

is the overdose penalty parameter, $$\lambda_i^- \geq 0$$

is the underdose penalty parameter, $\hat{d}_i \geq 0$ is the prescribed dose for the i-th VOI, and $H(d_i - \hat{d}_i):R \rightarrow \{0,1\}$ is the Heaviside function defined as $$H(d_i - \hat{d}_i) = \begin{cases} 1, & \text{if } d_i - \hat{d}_i \\ 0, & \text{otherwise} \end{cases} . \tag{3}$$

7

The overdose penalty parameter $$\lambda_i^+$$

is positive if the i-th voxel belongs to OARs, or zero if the i-th voxel belongs to HR-CTV. The underdose parameter $$\lambda_i^-$$

is positive if the i-th voxel belongs to the HR-CTV, or zero if the i-th voxel belongs to the OARs. The function $\|t\|_{TV}$: $R^{np} \to R$ is defined as $$\|t\|_{TV} = \sum_{i=1}^{np-1} \left| t_{i+1} - t_i \right|,$$

and by defining $$L = \begin{bmatrix} -1 & 1 & 0 & 0 & \dots & 0 & 0 \\ 0 & -1 & 1 & 0 & \dots & 0 & 1 \\ \vdots & \vdots & \vdots & \vdots & \ddots & \vdots & \vdots \\ 0 & 0 & 0 & 0 & \dots & -1 & 1 \end{bmatrix} \in R^{(np-1) \times np} \qquad (4)$$

we obtain $\|t\|_{TV} = \|Lt\|_1$. The function $$\|t\|_{2,1} = \sum_{U=1}^{P} \|t[u]\|_2,$$

with $\|t[u]\|_2$ being the Euclidean norm, i.e., $$\|t[u]\|_2 = \sqrt{\sum_{j=1}^{n} (t[u])_j^2}.$$

We used the $(t[u])_j$ to denote the j-th element of vector $t[u]$. The block sparsity regularization term $\|t\|_{2,1}$ enables iterative removal of low-importance needles.

(2) Solve Needle Selection Optimization Via Proximal Operator Graph Solver

In this section, we present an efficient algorithm for solving (1) via proximal operator graph solver (POGS).[31] Several algorithms based POGS have been previously presented solving treatment planning optimization problems.[17,20,21] The key is to convert our problem (1) to an optimization with graph constraints and derive the proximators of the objective functions. Once these are done, we follow the same ideas as we did in our previous work to iteratively find the optimal solution.[17,20,21]

We define $$y_d, y_l, \text{ and } y \text{ as } y_d = Dt \in R^m, \ y_l = Lt \in R^{np-1}, \ y = \begin{bmatrix} y_d^T & y_l^T \end{bmatrix}^T.$$

Then we can reformulate the problem (1) as $$\min_{t,y}(g(y) + f(t)) \text{ s.t. } \begin{bmatrix} L \\ D \end{bmatrix} t = \begin{bmatrix} y_l \\ y_d \end{bmatrix} \qquad (6)$$

8 where $g(y):R^{np-1+m} \to R$ is defined as $g(y) = (y_d - \hat{d})^T \Lambda (y_d - \hat{d})^T + \beta \|y_l\|_1$ and $f(t):R^{np} \to R$ is define as $f(t) = \gamma \|t\|_{2,1}$, $t > 0$.

From the definition of the proximator of a function $f(t)$ at a point v, i.e., $$prox_f(v) = \text{argmin}_{t \in dom(f)} \left( f(t) + \frac{\rho}{2} \|t - v\|^2 \right) \qquad (7)$$

Where $\rho > 0$ is a parameter and $dom(f)$ is the domain of, we can obtain the proximator for the function $f(t)$ at $v \in R^{np}$ as $$prox_f(v) = \text{argmin}_{t \ge 0} \left( \gamma \|t\|_{2,1} + \frac{\rho}{2} \|t - v\|^2 \right) = \begin{bmatrix} \vdots \\ \max(\theta_u v[u], 0) \\ \vdots \end{bmatrix}, \qquad (8)$$

where, $$\theta_u = \begin{cases} \dfrac{\|v[u]\|_2 - \dfrac{\gamma}{\rho}}{\|v[u]\|_2}, & \|v[u]\|_2 > \dfrac{\gamma}{\rho}, u = 1, 2, \dots, p. \\ 0, & \text{otherwise} \end{cases} \qquad (9)$$

The proximator of $g(y)$ at $$v = \begin{bmatrix} v_l^T & v_d^T \end{bmatrix}^T \in R^{np-1+m}$$

with $v_l \in R^{np-1}$ and $v_d \in R^m$ can be obtained via $$prox_g(v) = \text{argmin}_y \left( (y_d - \hat{d})^T \Lambda (y_d - \hat{d})^T + \beta \|y_l\|_1 + \frac{\rho}{2} \|y - v\|_2^2 \right) = \qquad (10)$$

$$\begin{bmatrix} S_{\frac{\beta}{\rho}}(v_1) \\ y_d^* \end{bmatrix}, \ S_{\frac{\beta}{\rho}}(v_1):R^{np-1} \to R^{np-1} S_{\frac{\beta}{\rho}}(v_1) y_d^*$$

where is an element-wise functio $$S_{\frac{\beta}{\rho}}(v_1):R^{np-1} \to R^{np-1} S_{\frac{\beta}{\rho}}(v_1) y_d^* n.$$

The k-th element of and the i-th element of are defined as $$\left( S_{\frac{\beta}{\rho}}(v_1) \right)_k = \begin{cases} (v_l)_k - \dfrac{\beta}{\rho}, & \text{if } (v_l)_k > \dfrac{\beta}{\rho}, \\ 0, & \text{if } |(v_l)_k| < \dfrac{\beta}{\rho}, O_i = \\ (v_l)_k + \dfrac{\beta}{\rho}, & \text{if } (v_l)_k < -\dfrac{\beta}{\rho} \end{cases}$$

(3) Optimal Treatment Planning with Optimally Selected Needles

Solving optimization problem (1) provides an initial estimate of $t \in R^{np}$, and the delivery time spent on the u-th needle is the sum of all the elements of $t[u] \in R^n$. The number of optimal needles allowed, $k(k \le p)$, can be set by accepting k needles which take up most of the total delivery time after taking into considerations needle redistribution.

More specifically, the optimized dwell times for the entire needle set were sorted by total dwell time for each needle and the number of desired needles for each case was selected. For the selected needles, the geometric quadrant indices were analyzed to ensure each quadrant contained a minimum of ⅛$^{th}$ of the total number of selected needles. If a geometric quadrant contained an insufficient number of selected needles according to this criterion, then an iterative process was performed to ensure each quadrant was covered by sufficient needles. The needle with the lowest total dwell time in the selected group outside of the unfilled quadrant was replaced by the needle with the largest non-zero total dwell time from the post-optimization needle group that did not originally get selected. This process was repeated until the unfilled quadrant contained the required number of needles. The needle number criterion for each quadrant was re-checked and if any other needle quadrants did not meet criteria this process was repeated until all quadrants contained sufficient needle numbers.

Suppose after the selection of needles, the k needles which achieved the highest total amount of delivery time are specified by index set $\{u_1, u_2, \ldots, u_k\} \subseteq \{1, 2, \ldots, p\}$. An optimized treatment plan with the selected needles is then obtained by solving (1) with $\gamma=0$. This problem can be easily solved via the proximal operator graph solver.[17,20,21,30]

baselines. We directly use all the clinical needles for treatment planning optimization, and the corresponding results are presented in Table 1. HDR-BT (Escalation) and RSBT Base. (Escalation) refer to the optimized treatment plans for HDR-BT without needle selection (HDR-BT) and RSBT without needle selection (RSBT), respectively, with the dose escalation goal. HDR-BT (Sparing) and RSBT Base. (Sparing) refer to the optimized treatment plans for HDR-BT and RSBT with the urethra sparing goal, respectively. From the results, we can see that under the dose escalation goal, RSBT can improve the PTV $D_{90\%}$ over HDR-BT by 30.2%±3.8%, while reducing the number of needles by 10.5%±6.3%, and the cost for these benefits is the longer treatment time, i.e., which was increased by 212.0%±56.4%. Under urethra sparing goal, RSBT can reduce the urethra $D_{10\%}$ of HDR-BT by 23.2%±2.3% and the number of needles by 10.5%±6.3% at a cost of 139.5%±43.6% increase in treatment time.

TABLE 1

Optimal treatment plans without needle selection. The treatment plan statistics presented are averaged over all the patient cases. The percentage is the change for RSBT relative to HDR-BT.

| # of Selected Needles | | | 20 | 18 | 16 | 14 | 12 | 10 |
|---|---|---|---|---|---|---|---|---|
| NEEPO | PTV | $D_{90\%}$ (Gy) | 31.3 ± 1.5 | 31.1 ± 1.6 | 30.7 ± 1.7 | 30.1 ± 2.3 | 29.4 ± 2.4 | 28.2 ± 2.3 |
| (Escalation) | | $V_{100}$ (%) | 99.4 ± 0.5 | 99.4 ± 0.4 | 99.4 ± 0.4 | 99.0 ± 2.1 | 98.7 ± 2.3 | 98.1 ± 2.8 |
| | | $V_{150}$ (%) | 80.1 ± 9.2 | 79.4 ± 9.3 | 77.9 ± 9.0 | 76.0 ± 11.0 | 72.9 ± 11.8 | 68.9 ± 10.8 |
| | | $V_{200}$ (%) | 28.2 ± 6.3 | 28.9 ± 6.5 | 30.0 ± 6.4 | 30.5 ± 6.4 | 31.5 ± 6.9 | 32.5 ± 6.6 |
| | Ureth | $D_{10\%}$ (Gy) | 21.2 ± 0.8 | 21.3 ± 0.7 | 21.5 ± 0.8 | 21.7 ± 0.7 | 22.0 ± 0.6 | 22.3 ± 0.5 |
| | | Mean | 21.6 ± 0.7 | 21.7 ± 0.7 | 21.8 ± 0.7 | 22.0 ± 0.6 | 22.3 ± 0.7 | 22.4 ± 0.7 |
| | Bladd | $D_{2cc}$ (Gy) | 14.8 ± 1.7 | 14.9 ± 1.7 | 15.1 ± 1.8 | 15.4 ± 1.5 | 15.6 ± 1.3 | 15.7 ± 1.4 |
| | Rectu | $D_{2cc}$ (Gy) | 8.2 ± 0.9 | 8.2 ± 0.9 | 8.3 ± 1.0 | 8.4 ± 1.1 | 8.4 ± 1.1 | 8.9 ± 1.9 |
| | | Treatment Time (min) | 47.3 ± 6.6 | 47.6 ± 6.6 | 48.5 ± 7.1 | 50.0 ± 8.2 | 50.7 ± 8.6 | 52.2 ± 9.3 |
| NEEP | PTV | $D_{90\%}$ (Gy) | 16.5 ± 0.0 | 16.5 ± 0.0 | 16.5 ± 0.0 | 16.5 ± 0.0 | 16.5 ± 0.0 | 16.5 ± 0.0 |

After the dwell time solution is obtained, dose-volume metrics for clinical evaluation of treatment plans can be calculated.

III. Results

We use 26 patient cases with prostate tumor sizes ranging from 43.5 cm³ to 92.7 cm³, with average and standard deviation being 65.5 cm³ and 14.6 cm³, respectively. The number of clinical needles in RSBT for each patient is 20, while that in HDR-BT ranges from 20 to 24. For NEEPO, the number of programmatically generated needles for each patient ranged from 37 to 85 with average and standard deviation being 57.8 and 11.4.

In the first set of simulations, we present the optimized treatment plans without using needle selection techniques as In the second set of simulations, we apply the needle selection to obtain optimized treatment plans with optimally selected needles. The optimized treatment plans with the optimally selected needles in the case with only programmatic needles for selection are presented in Table 2, while those in the case with both clinical and programmatic needles for selection are presented in Table 3. By comparing the results in two different scenarios, we can see that they do not differ much, meaning that the incorporation of needle positions manually selected by physician experts is unnecessary for NEEPO. For example, under the dose escalation goal with 20 optimally selected needles, the p-value between PTV $D_{90\%}$ in Table 2 and that in Table 3 is 0.93, which means that the PTV $D_{90\%}$ in both Table 2 and 3 highly likely come from normal distributions with same mean and same variance.

TABLE 2

NEEPO with needle pool consisting of only the programmatic needles. The treatment plan statistics are averaged over all the patient cases.

| # of Selected Needles | | | 20 | 18 | 16 | 14 | 12 | 10 |
|---|---|---|---|---|---|---|---|---|
| NEEPPPO | PTV | D90% (Gy) | 31.3 ± 1.5 | 31.1 ± 1.6 | 30.7 ± 1.7 | 30.1 ± 2.3 | 29.4 ± 2.4 | 28.2 ± 2.3 |
| (Escalation) | | V100 (%) | 99.4 ± 0.5 | 99.4 ± 0.4 | 99.4 ± 0.4 | 99.0 ± 2.1 | 98.7 ± 2.3 | 98.1 ± 2.8 |
| | | V150 (%) | 80.1 ± 9.2 | 79.4 ± 9.3 | 77.9 ± 9.0 | 76.0 ± 11.0 | 72.9 ± 11.8 | 68.9 ± 10.8 |
| | | V200 (%) | 28.2 ± 6.3 | 28.9 ± 6.5 | 30.0 ± 6.4 | 30.5 ± 6.4 | 31.5 ± 6.9 | 32.5 ± 6.6 |
| | Urethra | D10% (Gy) | 21.2 ± 0.8 | 21.3 ± 0.7 | 21.5 ± 0.8 | 21.7 ± 0.7 | 22.0 ± 0.6 | 22.3 ± 0.5 |
| | | Mean (Gy) | 21.6 ± 0.7 | 21.7 ± 0.7 | 21.8 ± 0.7 | 22.0 ± 0.6 | 22.3 ± 0.7 | 22.4 ± 0.7 |

TABLE 2-continued

NEEPO with needle pool consisting of only the programmatic needles. The
treatment plan statistics are averaged over all the patient cases.

| # of Selected Needles | | | 20 | 18 | 16 | 14 | 12 | 10 |
|---|---|---|---|---|---|---|---|---|
| | Bladder | D2cc (Gy) | 14.8 ± 1.7 | 14.9 ± 1.7 | 15.1 ± 1.8 | 15.4 ± 1.5 | 15.6 ± 1.3 | 15.7 ± 1.4 |
| | Rectum | D2cc (Gy) | 8.2 ± 0.9 | 8.2 ± 0.9 | 8.3 ± 1.0 | 8.4 ± 1.1 | 8.4 ± 1.1 | 8.9 ± 1.9 |
| | Treatment Time (min) | | 47.3 ± 6.6 | 47.6 ± 6.6 | 48.5 ± 7.1 | 50.0 ± 8.2 | 50.7 ± 8.6 | 52.2 ± 9.3 |
| NEEPO | PTV | D90% (Gy) | 16.5 ± 0.0 | 16.5 ± 0.0 | 16.5 ± 0.0 | 16.5 ± 0.0 | 16.5 ± 0.0 | 16.5 ± 0.0 |
| (Sparing) | | V100 (%) | 90.0 ± 0.0 | 90.0 ± 0.0 | 90.0 ± 0.0 | 90.0 ± 0.0 | 90.0 ± 0.0 | 90.0 ± 0.0 |
| | | V150 (%) | 24.0 ± 4.9 | 25.2 ± 5.2 | 27.6 ± 5.0 | 29.9 ± 5.9 | 33.3 ± 5.4 | 38.0 ± 6.6 |
| | | V200 (%) | 8.9 ± 2.5 | 9.7 ± 2.7 | 11.2 ± 2.7 | 12.9 ± 3.3 | 15.1 ± 3.1 | 18.7 ± 4.3 |
| | | D10% (Gy) | 11.2 ± 0.7 | 11.3 ± 0.7 | 11.6 ± 0.8 | 12.0 ± 1.2 | 12.4 ± 1.2 | 13.1 ± 1.3 |
| | Urethra | Mean (Gy) | 11.4 ± 0.6 | 11.5 ± 0.6 | 11.8 ± 0.7 | 12.1 ± 1.0 | 12.6 ± 1.1 | 13.2 ± 1.1 |
| | Bladder | D2cc (Gy) | 7.9 ± 1.2 | 8.0 ± 1.2 | 8.2 ± 1.2 | 8.5 ± 1.4 | 8.8 ± 1.3 | 9.3 ± 1.3 |
| | Rectum | D2cc (Gy) | 4.3 ± 0.6 | 4.4 ± 0.6 | 4.5 ± 0.6 | 4.6 ± 0.7 | 4.8 ± 0.8 | 5.3 ± 1.5 |
| | Treatment Time (min | | 25.1 ± 4.4 | 25.4 ± 4.5 | 26.3 ± 4.9 | 27.7 ± 6.7 | 28.8 ± 6.9 | 31.0 ± 7.5 |

TABLE 3

NEEPO with needle pool being the combination of clinical needles and
programmatic needles. The # of Pres. and the # of Prog. are the number of needles
selected from the clinical needle set and the programmatic needle set, respectively. The
treatment plan statistics are averaged over all the patient cases.

| # of Selected Needles | | | 20 | 18 | 16 | 14 | 12 | 10 |
|---|---|---|---|---|---|---|---|---|
| NEEPO | PTV | D90% (Gy) | 31.3 ± 1.0 | 31.1 ± 1.0 | 30.9 ± 1.1 | 30.5 ± 1.2 | 29.7 ± 1.7 | 28.8 ± 2.1 |
| (Escalation) | | V100 (%) | 99.5 ± 0.3 | 99.5 ± 0.3 | 99.5 ± 0.3 | 99.5 ± 0.4 | 99.2 ± 0.7 | 98.7 ± 1.3 |
| | | V150 (%) | 80.2 ± 6.7 | 79.8 ± 6.6 | 79.2 ± 6.4 | 77.4 ± 7.1 | 73.9 ± 9.5 | 70.7 ± 10.8 |
| | | V200 (%) | 26.4 ± 5.3 | 27.6 ± 5.8 | 28.7 ± 5.7 | 29.3 ± 5.3 | 29.3 ± 5.4 | 30.1 ± 4.9 |
| | Urethra | D10% (Gy) | 21.1 ± 0.6 | 21.3 ± 0.7 | 21.5 ± 0.8 | 21.7 ± 0.8 | 21.9 ± 0.8 | 22.1 ± 0.7 |
| | | Mean (Gy) | 21.5 ± 0.6 | 21.7 ± 0.7 | 21.9 ± 0.7 | 22.1 ± 0.8 | 22.2 ± 0.8 | 22.4 ± 0.8 |
| | Bladder | D2cc (Gy) | 14.7 ± 1.7 | 14.9 ± 1.7 | 15.2 ± 1.7 | 15.4 ± 1.7 | 15.7 ± 1.7 | 15.8 ± 1.6 |
| | Rectum | D2cc (Gy) | 8.1 ± 0.9 | 8.1 ± 0.9 | 8.3 ± 0.9 | 8.4 ± 1.0 | 8.5 ± 1.0 | 8.6 ± 1.2 |
| | Treatment Time (min) | | 46.8 ± 6.3 | 47.3 ± 6.3 | 48.2 ± 6.5 | 49.1 ± 7.4 | 50.4 ± 8.0 | 51.4 ± 8.3 |
| NEEPO | PTV | D90% (Gy) | 16.5 ± 0.0 | 16.5 ± 0.0 | 16.5 ± 0.0 | 16.5 ± 0.0 | 16.5 ± 0.0 | 16.5 ± 0.0 |
| (Sparing) | | V100 (%) | 90.0 ± 0.0 | 90.0 ± 0.0 | 90.0 ± 0.0 | 90.0 ± 0.0 | 90.0 ± 0.0 | 90.0 ± 0.0 |
| | | V150 (%) | 22.5 ± 3.6 | 24.2 ± 3.9 | 26.0 ± 4.0 | 27.8 ± 4.6 | 30.1 ± 5.2 | 33.7 ± 6.4 |
| | | V200 (%) | 8.0 ± 1.8 | 9.1 ± 1.9 | 10.3 ± 2.2 | 11.8 ± 2.7 | 13.5 ± 3.0 | 15.9 ± 4.1 |
| | Urethra | D10% (Gy) | 11.1 ± 0.5 | 11.3 ± 0.5 | 11.5 ± 0.6 | 11.8 ± 0.6 | 12.2 ± 0.8 | 12.7 ± 1.0 |
| | | Mean (Gy) | 11.4 ± 0.4 | 11.5 ± 0.4 | 11.7 ± 0.5 | 11.9 ± 0.5 | 12.4 ± 0.8 | 12.9 ± 0.9 |
| | Bladder | D2cc (Gy) | 7.8 ± 1.0 | 7.9 ± 1.1 | 8.1 ± 1.0 | 8.4 ± 1.0 | 8.7 ± 1.1 | 9.1 ± 1.2 |
| | Rectum | D2cc (Gy) | 4.3 ± 0.5 | 4.3 ± 0.5 | 4.4 ± 0.5 | 4.5 ± 0.6 | 4.7 ± 0.7 | 4.9 ± 0.8 |
| | Treatment Time (min) | | 24.8 ± 3.7 | 25.2 ± 3.9 | 25.8 ± 4.0 | 26.6 ± 4.5 | 28.1 ± 5.1 | 29.6 ± 5.6 |
| Needles Composition | # of Clini. | | 5.8 ± 2.6 | 5.3 ± 2.3 | 4.7 ± 2.1 | 4.3 ± 2.2 | 3.8 ± 1.9 | 3.3 ± 1.8 |
| | # of Prog. | | 14.2 ± 2.6 | 12.7 ± 2.3 | 11.3 ± 2.1 | 9.8 ± 2.2 | 8.2 ± 1.9 | 6.8 ± 1.8 |

In the third set of simulations, we present in FIG. 3A to FIG. 3D, the boxplots of the PTV D90% and the urethra D10% in the treatment plans of all the patients obtained by NEEPO. The 'R' and 'H' refer to the RSBT and HDR-BT baselines without needle selection, respectively. We can see that there is a steady increase in the PTV D90% when we increase the number of needles optimally selected, while the urethra D10% decreases steadily.

Figure 4:
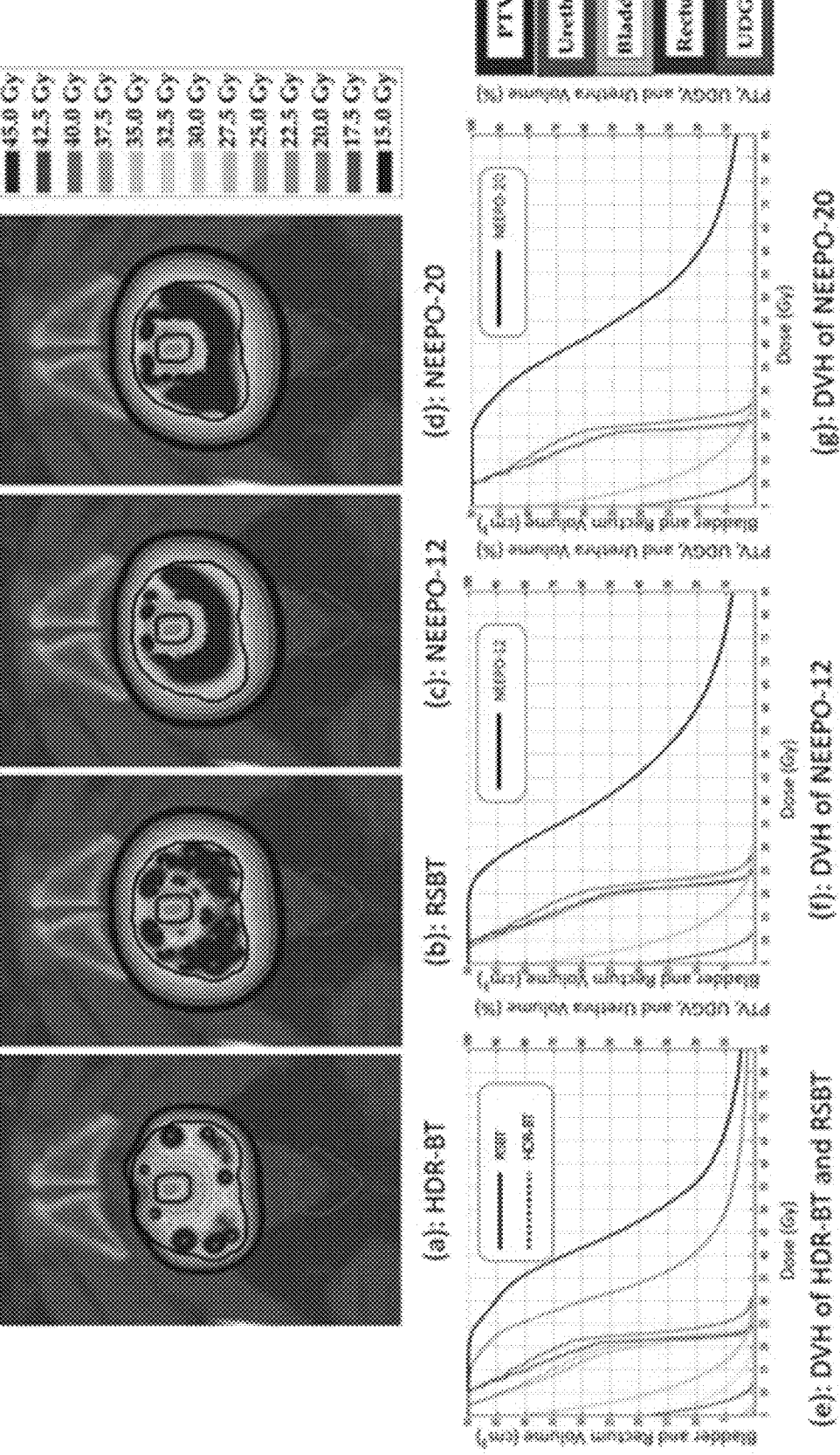
FIG. 4 with panels (a)-(g) illustrates dose distribution maps and DVHs of one patient case when only the programmatic needles are used for selection. In (a), HDR-BT achieves a PTV D90% of 22.6 Gy with 22 needles in 14.2 minutes. In (b), RSBT achieves a PTV D90% of 30.1 Gy using 20 needles in 47.1 minutes. In (c), NEEPO achieves a PTV D90% of 29.9 Gy using 12 optimally selected needles in 42.9 minutes. In (d), NEEPO achieves PTV D90% of 33.6 Gy using 20 optimally selected needles in 40.2 minutes. In (e), DVH of HDR-BT and RSBT. In (f), DVH of NEEPO with 12 optimally selected needles. In (g), DVH of NEEPO with 20 optimally selected needles.

In FIG. 4, we present in the dose distribution maps and dose-volume histograms (DVHs) under the dose escalation goal for a particular patient (the patient #19) to demonstrate the performance of our proposed method.

IV. Discussion

The proposed needle selection is motivated by the following two aspects. Firstly, we aim to automatically select an optimal set of needles to achieve treatment plans with high quality, e.g., improving the PTV $D_{90\%}$ under the dose escalation goal or reducing the urethra $D_{10\%}$ for the purpose of urethral sparing. Our second aim is to reduce the operational complexity in clinical practice, e.g., the complexity can be reduced while fewer needles need to be placed.

From the simulation results in Table 2 and 3, we see that the optimized treatment plans with optimally selected needles remain almost the same in both the case where only programmatic needles are used for selection and the case where both the clinical and programmatic needles are used for selection. This implies that NEEPO is able to automatically select an optimal set of needles for prostate RSBT treatment planning with no or minimal intervention/guidance from physicians. Since adding the clinical needles to the needle pool for selection barely brings benefits, one can simply prescribe a single basis needle for dwell positions and apply it to the selected needles by NEEPO, which removes the heavy burden on physicians for manually prescribing best needles by trial-and-error. Furthermore, it is contemplated that we can automatically generate the basis needle for dwell positions so that the system can be completely automated. An efficient algorithm may be used to optimize the number of dwell positions associated with each needle and optimize the spacing between neighboring dwell positions.

A feasible way for optimal needle selection with concurrent optimization on dwell positions can be done by introducing an extra $L_1$ regularization term to the objective function, that is $$\min_{d,t} h(d) + \beta \|t\|_{TV} + \gamma \|t\|_{2,1} + \delta \|t\|_1$$

$$\text{s.t. } Dt = d, \, t \geq 0,$$

where the $\delta > 0$ is a parameter for controlling the tradeoff between the $L_1$ regularization and the other terms in the objective function. The $\|t\|_1$ is simply the sum of all the absolute value of all the elements of t.

From the results in Tables 1, 2, and 3, we can see that RSBT modality may always require a much longer delivery time than HDR-BT, i.e., roughly two times of that with HDR-BT is needed for NEEPO using 20 optimally selected needles. This is because a partially shielded $^{169}$Yb radiation source emits a lower photon energy per unit time into the PTV than an unshielded $^{192}$Ir source, even if both the $^{169}$Yb (27 Ci) and $^{192}$Ir (10 Ci) sources have the same unshielded dose rates at 1 cm lateral to the source in water, which was the case for the simulated sources in the current work. The total delivery time will slightly increase as the number of needles allowed for delivery decreases. However, as the proposed NEEPO method can effectively reduce the number of needles needed, it will be able to substantially shorten the needle placement time, which may certainty alleviate the negative effect of the longer treatment time.

V. Conclusions

The NEEPO algorithm can improve RSBT dose escalation and urethra sparing, and substantially decrease the number of implanted needles needed to reach desired PTV $D_{90\%}$ and/or urethra $D_{10\%}$ levels. The PTV $V_{200\%}$ and delivery times increase as the needle number decreases would need to be considered in the needle reduction process, more so for urethra sparing than for dose escalation.

Although specific methodologies and systems have been shown and described herein, the present invention contemplates numerous options, variations, and alternatives. These include variations in the type of brachytherapy, the type of imaging devices used to acquire imagery, the number and type of radiation delivery devices, the number of potential needle positions, the parameters used for the optimization, and other variations. Therefore, the present invention is not to be limited to the specific embodiments shown and described herein.

The methods described herein or aspects thereof may be incorporated into software in the form of instructions stored on a non-transitory computer or machine readable medium. Thus, it is contemplated that existing treatment planning systems and brachytherapy systems may be reprogrammed to perform methods described herein. It is further to be understood that the methods described here may allow for use with portable imaging systems such as portable MRI systems which may be constructed specifically to work with the treatment planning system shown and described, such as to provide imagery which may be utilized in the brachytherapy planning.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments may be described herein as implementing mathematical methodologies including logic or a number of components, modules, or mechanisms. Modules may constitute either software modules (e.g., code embodied on a machine-readable medium or in a transmission signal) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules. Where the term "processor" is used, it is to be understood that it encompasses one or more processors whether located together or remote from one other.

Similarly, the methods described herein may be at least partially processor-implemented. For example, at least some of the operations of a method may be performed by one or processors or processor-implemented hardware modules. The performance of certain of the operations may be distributed among the one or more processors, not only residing within a single machine, but deployed across a number of machines. In some example embodiments, the processor or processors may be located in a single location (e.g., within a hospital, clinic, or medical office environment), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs).)

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, nonvolatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the disclosure. This description should be read to include one or at least one and the singular also includes the plural unless it is obvious that it is meant otherwise.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment or example.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function or "step for [perform]ing [a function] . . . ", it is intended that such elements are to be interpreted under 35 U.S.C. 112 § (f). However, for any claims containing elements designated in any other manner, it is intended that such elements are not to be interpreted under 35 U.S.C. § 112(f).

The invention is not to be limited to the particular embodiments described herein. In particular, the invention contemplates numerous variations in the specific methodology used with respect to the formation and solving of the optimization problem, its parameters, the terms included, and other variations. The foregoing description has been presented for purposes of illustration and description. It is not intended to be an exhaustive list or limit any of the invention to the precise forms disclosed. It is contemplated that other alternatives or exemplary aspects are considered included in the invention. The description is merely examples of embodiments, processes, or methods of the invention. It is understood that any other modifications, substitutions, and/or additions can be made, which are within the intended spirit and scope of the invention.

REFERENCES

1. Siegel R L, Miller K D, Fuchs H E, Jemal A. Cancer statistics, 2021. CA: a Cancer Journal for Clinicians. 2021; 71(1):7-33.
2. Yoshioka Y, Suzuki O, Isohashi F, et al. High-dose-rate brachytherapy as monotherapy for intermediate- and high-risk prostate cancer: clinical results for a median 8-year follow-up. Int J Radiat Oncol Biol Phys. 2016; 94: 675-682.
3. Liu J, Kaidu M, Sasamoto R, Ayukawa F, Yamana N, Sato H, Tanaka K, Kawaguchi G, Ohta A, Maruyama K, Abe E. Two-fraction high-dose-rate brachytherapy within a single day combined with external beam radiotherapy for prostate cancer: single institution experience and outcomes. Journal of radiation research. 2016 Jun. 1; 57(3): 280-7.
4. Morton G, McGuffin M, Chung H T, Tseng C L, Helou J, Ravi A, Cheung P, Szumacher E, Liu S, Chu W, Zhang L. Prostate high dose-rate brachytherapy as monotherapy for low and intermediate risk prostate cancer: Efficacy results from a randomized phase II clinical trial of one fraction of 19 Gy or two fractions of 13.5 Gy. Radiotherapy and Oncology. 2020; 146:90-6.12
5. Siddiqui Z A, Gustafson G S, Ye H, Martinez A A, Mitchell B, Sebastian E, Limbacher A, Krauss D J. Five-year outcomes of a single-institution prospective trial of 19-Gy single-fraction high-dose-rate brachytherapy for low-and intermediate-risk prostate cancer. International Journal of Radiation Oncology* Biology* Physics. 2019; 104(5):1038-44.
6. Prada P J, Cardenal J, Blanco A G, et al. High-dose-rate interstitial brachytherapy as monotherapy in one fraction for the treatment of favorable stage prostate cancer: Toxicity and long-term biochemical results. Radiother Oncol. 2016; 119: 411-416.
7. Kuban D A, Tucker S L, Dong L, et al. Long-term results of the M. D. Anderson randomized dose-escalation trial for prostate cancer. Int J Radiat Oncol Biol Phys. 2008; 70: 67-74.
8. Heemsbergen W D, Al-Mamgani A, Slot A, Dielwart M F, Lebesque J V. Long-term results of the Dutch randomized prostate cancer trial: impact of dose-escalation on local, biochemical, clinical failure, and survival. Radiother Oncol. 2014; 110: 104-109.
9. Martinez A A, Gonzalez J, Ye H, et al. Dose escalation improves cancer-related events at 10 years for intermediate- and high-risk prostate cancer patients treated with hypofractionated high-dose-rate boost and external beam radiotherapy. Int J Radiat Oncol Biol Phys. 2011; 79: 363-370.
10. Hsu I C, Hunt D, Straube W, et al. Dosimetric analysis of radiation therapy oncology group 0321: the importance of urethral dose. Pract Radiat Oncol. 2014; 4: 27-34.
11. Sullivan L, Williams S G, Tai K H, Foroudi F, Cleeve L, Duchesne G M. Urethral stricture following high dose rate brachytherapy for prostate cancer. Radiotherapy and Oncology. 2009; 91(2):232-236.
12. Hindson B R, Millar J L, Matheson B. Urethral strictures following high-dose-rate brachytherapy for prostate cancer: Analysis of risk factors. Brachytherapy. 2013; 12(1): 50-55.
13. Akimoto T, Katoh H, Noda S E, et al. Acute genitourinary toxicity after high dose rate (HDR) brachytherapy combined with hypofractionated external-beam radiation therapy for localized prostate cancer: second analysis to determine the correlation between the urethral dose in HDR brachytherapy and the severity of acute genitourinary toxicity. Int J Radiat Oncol Biol Phys. 2005; 63: 472-478.
14. Gomez-Iturriaga A, Casquero F, Pijoan J I, et al. Health-related-quality-of-life and toxicity after single fraction 19 Gy high-dose-rate prostate brachytherapy: Phase II trial. Radiother Oncol. 2017; 26: 278-282.
15. Mohammed N, Kestin L, Ghilezan M, et al. Comparison of acute and late toxicities for three modern high-dose radiation treatment techniques for localized prostate cancer. Int J Radiat Oncol Biol Phys. 2012; 82: 204-212.
16. Adams Q, Hopfensperger K M, Kim Y, et al. Effectiveness of rotating shield brachytherapy for prostate cancer dose escalation and urethral sparing. Int J Radiat Oncol Biol Phys. 2018; 102: 1543-1550.
17. Adams Q, Hopfensperger K M, Kim Y, Wu X, Flynn R T. 169Yb-based rotating shield brachytherapy for prostate cancer. Medical Physics. 2020 December; 47(12):6430-9.
18. Famulari G, Duclos M, Enger S A. A novel 169 Yb-based dynamic-shield intensity modulated brachytherapy delivery system for prostate cancer. Med Phys. 2020 March; 47(3):859-868.
19. Flynn R T, Adams Q E, Hopfensperger K M, Wu X, Xu W, Kim Y. Efficient (169) Yb high-dose-rate brachytherapy source production using reactivation. Med Phys. 2019; 46: 2935-2943.
20. Cho M, Wu X, Dadkhah H, Yi J, Flynn R T, Kim Y, Xu W. Fast dose optimization for rotating shield brachytherapy. Medical Physics. 2017 October; 44(10): 5384-92.
21. Yi J, Wu X, Adams Q, Hopfensperger K, Patwardhan K, Flynn R, Kim Y, Xu W. Optimized rotating shield brachytherapy treatment plan under treatment time budget. Medical Physics. 2019 June; 46(6):E562-E562.
22. Liu Y, Flynn R T, Yang W, Kim Y, Bhatia S K, Sun W, Wu X. Rapid emission angle selection for rotating-shield brachytherapy. Medical Physics. 2013 May; 40(5): 051720.
23. Liu Y, Flynn R T, Kim Y, Yang W, Wu X. Dynamic rotating-shield brachytherapy. Medical Physics. 2013 December; 40(12):121703.

24. Liu Y, Flynn R T, Kim Y, Dadkhah H, Bhatia S K, Buatti J M, Xu W, Wu X. Paddle-based rotating-shield brachytherapy. Medical Physics. 2015 October; 42(10): 5992-6003.

25. Dadkhah H, Hopfensperger K M, Kim Y, Wu X, Flynn R T. Multisource rotating shield brachytherapy apparatus for prostate cancer. Int J Radiat Oncol Biol Phys. 2017; 99: 719-728.

26. Ferrari G, Kazareski Y, Laca F, Testuri C E. A model for prostate brachytherapy planning with sources and needles position optimization. Operations Research for Health Care. 2014 Mar. 1; 3(1):31-9.

27. van der Meer M C, Pieters B R, Niatsetski Y, Alderliesten T, Bel A, Bosman P A. Better and faster catheter position optimization in HDR brachytherapy for prostate cancer using multi-objective real-valued GOMEA. InProceedings of the Genetic and Evolutionary Computation Conference 2018 Jul. 2 (pp. 1387-1394).

28. Siauw T, Cunha A, Berenson D, Atamtürk A, Hsu I C, Goldberg K, Pouliot J. NPIP: A skew line needle configuration optimization system for HDR brachytherapy. Medical physics. 2012 July; 39(7Part1):4339-46.

29. Wang C, Gonzalez Y, Shen C, Hrycushko B, Jia X. Simultaneous needle catheter selection and dwell time optimization for preplanning of high-dose-rate brachytherapy of prostate cancer. Physics in Medicine & Biology. 2021 Feb. 26; 66(5):055028.

30. Le A, Yi J, Kim Y, Flynn R, Xu W, Wu X. Keyway selection optimization for multi-helix rotating shield brachytherapy (H-RSBT). Medical Physics. 2018; 45(6): E159-E159.

31. Fougner C, Boyd S. Parameter selection and preconditioning for a graph form solver. In Emerging Applications of Control and Systems Theory 2018 (pp. 41-61). Springer, Cham.

What is claimed is:

1. A method for needle position optimization for prostate brachytherapy for use with a radiation delivery device configured to use a plurality of needles inserted into a prostate of a patient, the method comprising:

obtaining imagery of the prostate of the patient;

generating a needle pool for prostate brachytherapy treatment of the patient based on the imagery of the prostate of the patient;

determining at a computing device an optimum prostate brachytherapy treatment plan for the patient by iteratively removing needles from the needle pool by forming and computationally solving a convex optimization problem wherein the convex optimization problem uses a quadratic dosimetric penalty function, dwell time regularization by total variation, and a block sparsity regularization term; and performing the prostate brachytherapy according to the optimum prostate brachytherapy treatment plan for the patient.

2. The method of claim 1 wherein the imagery is magnetic resonance imagery.

3. The method of claim 1 wherein the obtaining the imagery of the prostate of the patient is performed using a portable magnetic resonance imaging (MRI) scanner.

4. The method of claim 1 wherein the computationally solving the convex optimization problem is performed using a proximal operator graph solver (POGS).

5. The method of claim 1 wherein the prostate brachytherapy is prostate rotating shield brachytherapy (RSBT).

6. The method of claim 1 wherein the prostate brachytherapy is high-dose-rate brachytherapy (HDR-BT).

7. The method of claim 1 wherein the convex optimization problem includes a dose escalation goal and a urethra sparing goal.

8. A radiation treatment planning system for prostate brachytherapy for use with a radiation delivery device configured to use a plurality of needles inserted into a prostate of a patient, the radiation treatment planning system comprising:

a processor;

a memory operatively connected to the processor having instructions stored thereon for execution by the processor to:

obtain imagery of the prostate of the patient;

generate a needle pool for prostate brachytherapy treatment of the patient based on the imagery of the prostate of the patient;

determine an optimum prostate brachytherapy treatment plan for the patient by iteratively removing needles from the needle pool by forming and computationally solving a convex optimization problem wherein the convex optimization problem uses a quadratic dosimetric penalty function, dwell time regularization by total variation, and a block sparsity regularization term; and generate an output for conveying the optimum prostate brachytherapy treatment plan to the radiation delivery device.

9. The radiation treatment planning system of claim 8 wherein the output is in a human-readable form conveying the optimum prostate brachytherapy treatment plan for the patient.

10. The radiation treatment planning system of claim 8 wherein the imagery is magnetic resonance imagery.

11. The radiation treatment planning system of claim 8 wherein the imagery of the prostate of the patient is obtained from a portable magnetic resonance imaging (MRI) scanner.

12. The radiation treatment planning system of claim 8 wherein the computationally solving the convex optimization problem is performed using a proximal operator graph solver (POGS).

13. The radiation treatment planning system of claim 8 wherein the prostate brachytherapy is prostate rotating shield brachytherapy (RSBT).

14. The radiation treatment planning system of claim 8 wherein the prostate brachytherapy is high-dose-rate brachytherapy (HDR-BT).

15. The radiation treatment planning system of claim 8 wherein the convex optimization problem includes a dose escalation goal and a urethra sparing goal.

16. A system for prostate brachytherapy comprising:

a plurality of needles;

a radiation delivery device configured to deliver radiation according to an optimum prostate brachytherapy treatment plan to use the plurality of needles when inserted into a prostate of a patient to delivery radiation thereto;

a processor;

a memory operatively connected to the processor having instructions stored thereon for execution by the processor to:

obtain imagery of the prostate of the patient;

generate a needle pool for prostate brachytherapy treatment of the patient based on the imagery of the prostate of the patient; and determine the optimum prostate brachytherapy treatment plan for the patient by iteratively removing needles from the needle pool by forming and computationally solving a convex optimization problem wherein the convex optimization problem uses a quadratic dosimetric penalty function, dwell time regularization by total variation, and a block sparsity regularization term;

generate an output conveying the optimum prostrate brachytherapy treatment plan to the radiation delivery device to deliver radiation according to the optimum prostate brachytherapy treatment plan.

17. The system of claim 16 further comprising an imaging device for acquiring the imagery of the prostate.

18. The system of claim 17 wherein the imaging device is a magnetic resonance imaging (MRI) scanner.

\* \* \* \* \*